United States Patent [19]

Jacobson et al.

[11] Patent Number: 5,284,834
[45] Date of Patent: * Feb. 8, 1994

[54] ADENOSINE FUNCTIONALIZED CONGENERS AS CARDIOVASCULAR TREATING AGENTS FOR ANIMALS AND METHODS FOR USING SAME

[75] Inventors: Kenneth A. Jacobson, Silver Spring; Kenneth L. Kirk, Bethesda, both of Md.; John W. Daly, Washington, D.C.

[73] Assignee: The United States of America as represented by the Secretary of the Department of Health and Human Services, Washington, D.C.

[*] Notice: The portion of the term of this patent subsequent to Nov. 6, 2007 has been disclaimed.

[21] Appl. No.: 924,792

[22] Filed: Aug. 6, 1992

Related U.S. Application Data

[63] Continuation of Ser. No. 346,257, May 1, 1989, abandoned, which is a continuation of Ser. No. 833,035, Feb. 26, 1986, abandoned, which is a continuation-in-part of Ser. No. 717,624, Mar. 29, 1985, abandoned.

[51] Int. Cl.$^5$ .................. A61K 31/52; C07H 17/00
[52] U.S. Cl. ................... 514/46; 536/27.6; 536/27.61; 536/27.62; 530/330; 530/331; 530/332; 514/17; 514/18; 514/19
[58] Field of Search .............. 536/27, 28, 29, 27.6, 536/27.62, 27.61; 514/46, 17, 18, 19, 46; 530/330, 331, 329, 332

[56] References Cited

U.S. PATENT DOCUMENTS

| | | | |
|---|---|---|---|
| 3,471,472 | 10/1969 | Thiel et al. | 536/27.62 |
| 3,502,649 | 3/1970 | Thiel et al. | 536/27.62 |
| 3,506,643 | 4/1970 | Thiel et al. | 536/27.62 |
| 3,551,409 | 12/1970 | Kampe et al. | 536/27.63 |
| 3,845,035 | 10/1974 | Kampe et al. | 536/27.61 |
| 3,851,056 | 11/1974 | Stork et al. | 514/46 |
| 3,914,415 | 10/1975 | Stein et al. | 514/46 |
| 4,340,730 | 2/1982 | Henderson et al. | 536/27.62 |
| 4,843,066 | 6/1989 | Yamada et al. | 514/45 |
| 4,968,672 | 11/1990 | Jacobson et al. | 514/46 |

*Primary Examiner*—Johnnie R. Brown
*Assistant Examiner*—J. Oliver Wilson
*Attorney, Agent, or Firm*—Leydig, Voit & Mayer, Ltd.

[57] ABSTRACT

This invention comprises a series of $N^6$-substituted adenosine analogues bearing functionalized chains for the covalent attachment to probes or solid supports. In these compounds coronary vasodilation in the open thorax dog model, typical of $A_2$-adenosine receptor agonists, is shown. The potency is modulated by distal structural changes in the chain, with the highest $A_2$-potency observed for two methylamides, a primary amine congener, and a biotin conjugate. These compounds have antihypertensive activity and certain components are charged and are excluded from crossing the blood-brain barrier.

43 Claims, No Drawings

ADENOSINE FUNCTIONALIZED CONGENERS AS CARDIOVASCULAR TREATING AGENTS FOR ANIMALS AND METHODS FOR USING SAME

This is a continuation of copending patent application Ser. No. 07/346,257, filed on May 1, 1989, now abandoned, which is a continuation of copending patent application Ser. No. 06/833,035, filed on Feb. 26, 1986, now abandoned, which is a continuation-in-part of copending patent application Ser. No. 06/717,624, filed on Mar. 29, 1985, now abandoned.

BACKGROUND OF THE INVENTION

Adenosine acts as a modulator of numerous physiological functions through two classes of extracellular membrane-bound receptors. The A1- and A2-adenosine receptors, currently delineated in different tissues according to the rank order of potency of certain adenosine analogues, are in general linked to adenylate cyclase in either an inhibitor ($A_1$) or a stimulatory ($A_2$) manner.

In this invention, the following abbreviations are used: $N^6$-R-1-phenyl-2-propyladenosine is R-PIA; $N^6$-cyclohexyladenosine is CHA; N-ethyladenosine-5'-uronamide is NECA.

At $A_1$-receptors the order of potency is R-PIA, CHA > NECA > S-PIA, while at $A_2$-receptors NECA is clearly the most potent. The $A_2$-adenosine receptor is associated with vasodilation producing a lowering of blood pressure, inhibition of platelet aggregation, and the antidiuretic effect of adenosine, and other physiological effects.

Adenosine analogues substituted at $N^6$ with spacer arms designed for attachment to soluble macromolecules or to solid supports for affinity chromatography are agonists at the $A_2$-adenosine receptor that mediates coronary vasodilation in the dog. The most active analogues have spacer arms terminating in —$NH_2$, —$NHCH_3$ or in a biotin residue. Comparisons of coronary vasoactivity with affinity for brain $A_1$ adenosine receptors identified one biotin-containing analogue as relatively selective for coronary $A_2$ receptors. The complex of this analogue with avidin retains coronary vasoactivity.

There has been noted a "functionalized congener" approach to the design of adenosine receptor ligands, utilizing a regioselectively incorporated spacer chain. The potency of binding at the $A_1$-receptor in rat cerebral cortical membranes is modulated by the presence of various attached groups or "carriers" linked to the chain through a stable covalent bond. This set of functionalized congeners is designed through a strategy of stepwise chain elongation in which intermediate structures were screened for potency to select structural elements which promote receptor binding. The purpose of this congener approach includes the identification of new animal therapeutic agents.

MATERIAL INFORMATION DISCLOSURE

The following U.S. patents are $N_6$-substituted adenosine derivatives having coronary dynamic activity: U.S. Pat. No. 3,471,472 Thiel et al; U.S. Pat. No. 3,502,649 Thiel et al; U.S. Pat. No. 3,506,643 Thiel et al; and U.S. Pat. No. 3,845,035 Kampe et al.

SUMMARY OF THE INVENTION

In the present invention there is compared the $A_1$- and $A_2$-potencies of a series of long-chain derivatives of adenosine suitable for attachment to "carriers," such as peptides or proteins, and for immobilization to polymeric matrices for affinity chromatography of adenosine receptors. The method employed is a comparison of increasing coronary blood flow via activation of an $A_2$-adenosine receptor versus an $A_1$-binding assay in rat brain. This method has been used recently to evaluate the selectivity of a series of 145 $N^6$-substituted adenosine analogues.

The compounds of the present invention which are used for treating animals and achieving coronary vasodilation are selected from the following formula.

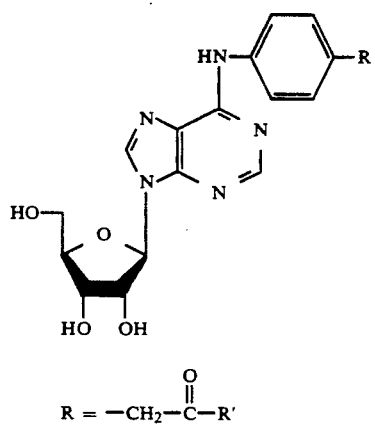

$$R = -CH_2-\overset{O}{\underset{\|}{C}}-R'$$

wherein R' is hydroxyl, lower alkylamino, monoarylamino (alkyl or aryl groups are optionally substituted with methyl, halolower alkyl, lower alkyl, ester, or amino groups), or an oligopeptide (up to five amino acids in length, optionally protected on the α-amino and α-carboxylate funtionality by conventional peptide blocking groups) in which the point of attachment is through an amide bond at the p-position of phenylalanine;

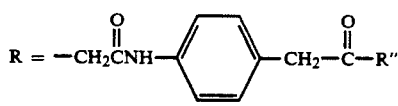

wherein R" is alkoxy, lower alkylamino (optionally substituted with amino or acylamino groups) or

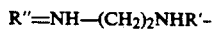

wherein
R''' is an acyl group including acetyl or p-hydroxyphenylpropionyl or di-biotinyl or α-bromoacetyl methyl fumaryl, d-biotinyl-ε-aminocaproyl, or an amino acid of the L- or D-configuration, or
R''' is a monoaryl group, or
R" is $NH(CH)_2N=C=S$.

Preferred compounds of the present invention are selected from Table 1 below. Compounds 1, 2, 4, and 5

(NECA, 2-chloroadenosine, R-PIA, and CHA) are commercially available from Research Biochemicals, Inc. (Natick, Mass.). The adenosine analogues u-19 were prepared and were characterized by elemental analysis, 300 MHz proton NMR, and californium plasma desorption mass spectrometry.

Among the adenosine functionalized congeners and derivatives are potent coronary vasodilators (see Table 1). Thus, the derivatives behave as $A_2$-agonists, with potency in some cases exceeding that of adenosine by up to an order of magnitude. The efficacy at $A_2$-receptors varied, depending on distal structural features of the chain attached at the para-position of the phenyl ring of $N^6$-phenyladenosine. Similarly, the novel adenosine derivatives (compounds 8-19) were previously reported, *J. Med. Chem.* 28:1341 (1985), to be specific competitive inhibitors of the binding of [$^3$H]CHA to $A_1$-receptors on rat cerebral cortical membranes.

Table 1 summarizes the experimental observations and comparisons of $A_1$ and $A_2$ adenosine receptors. The potency rank order of analogues 1-5 identifies the coronary adenosine receptor as an $A_2$ receptor. The results with analogues 6 and 7 show that $N^6$-phenyladenosines can exhibit some activity at this $A_2$-receptor. Our invention relates to the finding that certain functionalized ligands having spacer arms extending from an $N^6$-phenyl group have enhanced activity on vascular $A_2$ receptors and thus are effective anti-hypertensive agents.

All of the functionalized ligands except $N^6$-(4-carboxymethylphenyl)adenosine, 8, were potent coronary vasodilators, having MPRs versus adenosine ranging between 7 and 10. Although the most active analogue, 19, also had the largest $N^6$ substituent, there was no correlation between activity and size of the substitutent.

TABLE 1

Potency of Adenosine Analogues at a Coronary $A_2$-Adenosine Receptor and at a Brain $A_1$-Receptor

| Analogue | $A_2$ Receptor | | $A_1$ Receptor | MPR ($A_2$) / MPR ($A_1$) |
|---|---|---|---|---|
| | MPR Relative to Ado | MPR[a] Relative to MeAdo | MPR[a,b] Relative to MeAdo | |
| 1 N-Ethyladenosine-5'-uronamide (NECA) | 150 | 3000 | 12 | 250 |
| 2 2-Chloroadenosine | 27 | 540 | 10 | 54 |
| 3 $N^6$-methyladenosine | 0.05 | 1.0 | 1.0 | 1.0 |
| 4 $N^6$-R-1-Phenyl-2-propyladenosine (R-PIA) | 4.3 | 86 | 50 | 1.7 |
| 5 $N^6$-cyclohexyladenosine (CHA) | 1.6 | 32 | 71 | 0.45 |
| 6 $N^6$-phenyladenosine | 1.4 | 28 | 18 | 1.6 |
| 7 $N^6$-p-tolyladenosine | 1.35 | 27 | 24 | 1.1 |

[Structure of adenosine derivative with $NH$-phenyl-$CH_2CO$-R substituent at $N^6$ position]

R =
8 OH — [27% @ 21 μM][c] — 0.29 —
9 NHCH$_3$ — 4.9 ± 1.3 — 98 — 3.8 — 26

10 NH—[phenyl]—CH$_3$ — 2.1 ± 1.3 — 42 — 35 — 1.2

11 NH—[phenyl]—CH$_2$–CH(NHCOCF$_3$)(CO$_2$CH$_3$) — 3.0 ± 0.7 — 60 — 3.3 — 18

12 NH—[phenyl]—CH$_2$–CH(NHCOOC(CH$_3$)$_3$)(CONHCH$_2$CONHCH$_3$) — 4.4 ± 0.4 — 88 — 4.6 — 19

R = NH—[phenyl]—CH$_2$COR'

R' =
13 OCH$_3$ — 33.2 ± 1.6 — 64 — 24 — 2.7

TABLE 1-continued

Potency of Adenosine Analogues at a Coronary
$A_2$-Adenosine Receptor and at a Brain $A_1$-Receptor.

| Analogue | $A_2$ Receptor MPR Relative to Ado | $A_2$ Receptor MPR[a] Relative to MeAdo | $A_1$ Receptor MPR[a,b] Relative to MeAdo | $\dfrac{\text{MPR }(A_2)}{\text{MPR }(A_1)}$ |
|---|---|---|---|---|
| 14 NHCH$_3$ | 7.2 ± 1.3 | 144 | 9.0 | 16 |
| 15 NHNH$_2$ | 3.5 ± 0.8 | 70 | 13 | 5.3 |
| 16 NH(CH$_2$)$_2$NH$_2$ | 7.8 ± 2.5 | 156 | 71 | 2.2 |
| 17 NH(CH$_2$)$_2$NHCO(CH$_2$)$_2$—⟨phenyl⟩—OH | 2.8 ± 0.1 | 56 | 13 | 4.2 |
| 18 NH(CH$_2$)$_2$NH—CO∼biotin | 3.0 ± 0.2 | 60 | 5.5 | 11 |
| 19 NH(CH$_2$)$_2$NHCO(CH$_2$)$_5$NH—CO∼biotin | 10.2 ± 7.3 | 204 | 3.3 | 61 |

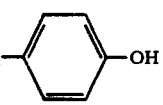

[a]Molar potency ratio relative to N$^6$-methyladenosine, which is set equal to 1.0.
[b]Molar potency ratio relative to adenosine, derived from K$_i$ values for antagonism of binding of 1nM [$^3$H]N$^6$-cyclohexyladenosine to rat cerebral cortical membranes.
[c]Highest concentration of analogue did not raise coronary blood flow to a level × 50% of maximum possible increase. In such a case % increase in flow over control is reported at the plasma nucleoside concentration achieved during infusion.

The spacer arms of the three most active analogues 14, 16 and 19, terminated, respectively, in an —NH$_2$ group, in an —NHCH$_3$ group, and a biotin residue. Coronary vasoactivity appeared to be independent of whether the spacer arm contained one phenyl residue (analogue 9) or two (analogues 10–19).

In order to provide a common index of potency on which to judge selectivity of $A_1$ and $A_2$ receptors, the coronary vasoactivity of analogues 9–19 was expressed as the MPR versus N$^6$-methyladenosine rather than adenosine. An $A_2/A_1$ potency ratio greater than 10 in such a direct comparison identified analogues 9, 11, 12, 14, 18 and 19 as relatively selective for $A_2$ receptors. Indeed, this comparison showed that none of the analogues was particularly selective for $A_1$ receptors; the least selective agonist at the $A_2$ receptor, 10, still had an $A_2/A_1$ potency ratio of 1.2. Attributes of a spacer arm which might contribute to selectivity for the $A_2$ receptor are branching beta to the distal phenyl ring (analogues 11 and 12), which pattern of branching is poorly tolerated by $A_1$ receptors, and termination in a biotin residue (analogue 18 and 19).

The intracoronary infusion of the complex of analogue 19 with avidin caused dose-dependent coronary vasodilation in each of two dogs. In contrast, analogue 18+avidin conjugate was inactive in this system, suggesting the requirement of the ε-aminocaproyl spacer unit for accessibility of the pharmacophore at the $A_2$-receptor site. Avidin by itself lacked coronary vasoactivity. The MPR versus adenosine of the analogue 19+avidin complex was 2.1±0.40, somewhat lower than that of 19, which was 10.2±7.3. Possible reasons for the reduced potency of 19 when bound to avidin include poor penetration of the avidin molecule (MW 66,000) into the cardiac intersitial space, steric hindrance exerted by the avidin molecule that impairs interaction of 19 with the receptor and loss of the contribution to binding affinity made by the spacer arm which, when anchored to the avidin molecule, may not be able to interact with the receptor. Unlike 19, which is practically insoluble in water and precipitated when stock solutions in the dimethyl sulfoxide were diluted for intracoronary infusion, the complex of 19 with avidin is quite soluble. Following intracoronary infusion of the 19+avidin complex, vasodilation was evident within 1–2 minutes, an onset of activation somewhat slower than the 20–30 seconds observed for 19. The retarded onset doubtless reflects the reduced rate at which avidin crosses the coronary capillary wall. Unlike the prolonged vasodilation caused by 19, which often lasted for an hour or more, the effect of the 19+avidin complex dissipated within 20 minutes. The vasoactivity of this macromolecular conjugate supports previous studies which showed an adenosine receptor to be located on the surface of coronary smooth muscle.

The potencies at $A_2$-receptors (Table 1) are expressed as a molar potency ratio of the EC$_{50}$ value of adenosine divided by that of the adenosine analogue. A common reference compound on which to base molar potency ratios was needed to facilitate comparison of activities at $A_1$ and $A_2$ receptors. Adenosine itself cannot be used as a reference in the $A_1$ binding assay since treatment of the membranes with adenosine deaminase is essential. N$^6$-Methyladenosine (MeAdo), the simplest N$^6$-substituted homologue, is active, although markedly weaker than adenosine (at least 10-fold at $A_1$-receptors and 20-fold at $A_2$-receptors), in both systems, and is a very poor substrate for adenosine deaminase. Thus, MeAdo was used as a suitable reference compound.

The novel adenosine analogues consist of derivatives of a carboxylic acid congener, 8, and an amino congener, 16. The derivatives have been synthesized from these functionalized congeners mainly through mild carbodiimide and active ester amide-forming reactions.

BIOLOGICAL ACTIVITY

As previously noted, NECA and, to a lesser extent, 2-chloroadenosine were exceptionally potent in the coronary $A_2$-assay. Simple N$^6$-substituted adenosines (5–7), which are selective for $A_1$-adenosine receptors in other systems, were much less potent.

The carboxylic acid congener, 8, was only weakly active as a coronary vasodilator and in the $A_1$-binding assay. In contrast, simple amide derivatives of this carboxylic acid, such as 9 and 10, showed enhanced activity at both receptor subtypes. Overall, derivatives of 8 which are either neutral or positively charged showed molar potency ratios over MeAdo of between 40 and 200, thus all were more potent than adenosine at the $A_2$-receptor. Several compounds, two methylamides (9 and 14), the primary amino congener (16), and a biotin complex containing an ε-aminocaproyl linkage (19), had notably high potency (MPR relative to MeAdo was 100 or greater) at $A_2$ receptors.

Potencies of particular compounds were in some cases highly divergent at $A_1$ and $A_2$ receptors, suggesting receptor subtype selectivity (e.g., 9, 14, 18, and 19). The rise in $A_2$ potency upon blocking the carboxylic acid congener as a methylamide, 9, was more substantial relative to the gain in $A_1$ potency. Thus, this compound showed an $A_2$ selectivity in the middle range between the selectivity of the traditional $N^6$-unsubstituted $A_2$-agonists, NECA and 2-chloroadenosine, and the nonselective, simple $N^6$-substituted adenosines (e.g., 5–7). The primary amino congener, 16 was not $A_2$-selective, since the high efficacy as a coronary vasodilator was paralleled by a high potency at the $A_1$-receptor. On the other hand, the two conjugates of p-aminophenylalanine showed moderate activity at $A_2$-receptors, approximately equal to that of R-PIA, accompanied by relatively low potency at $A_1$ receptors. Comparison of the peptide derivatives with the p-toluide, 10, it seems that branching at the position beta to the distal phenyl ring introduces bulk which is not well tolerated at the $A_1$-receptor but is compatible with high potency at the $A_2$ receptor.

A. The compounds were also active in other tests of $A_2$-adenosine receptor activity, e.g., stimulation of adenylate cyclase in human platelet membranes, with the following IC50 values:

| Compound | |
|---|---|
| 4 | 3.1 μM |
| 8 | 26. μM |
| 16 | 0.98 μM |
| 19 | 2.4 μM |

B. Certain of the conjugates have ionizable groups on the attached chain. These groups alter the biodistribution of the compounds and make them less likely to enter the brain and produce central depressant effects. The effect of charged groups is reflected in octanol water partition coefficients as follows:

| Compound | $\log P \left( \dfrac{\text{octanol}}{\text{pH 7.2, 0.01 phosphate}} \right)$ |
|---|---|
| 4 | 2.0 |
| 8 | less than −1.4 |
| 16 | −0.81 |

Compound 4 enters the brain and produces central side effects. Compounds 8 and 16 are considerably more polar than 4. The biodistribution may be studied using tritiated analogs (see examples).

EXAMPLE

The assay of coronary vasoactivity in the anesthetized, open-chest dog, is described by Kusachi et al, J. Med. Chem., in press, and Olsson, et al, J. Circ. Res. 45:468–478 (1979). The assay estimates an EC-50, the concentration of analogue which produces a half maximum change in coronary conductance (reciprocal resistance). To reduce between-animal variability activity is expressed as a molar potency ratio (MPR) the value of the EC-50 of adenosine divided by that of the analogue. Owing to the low water solubility of some of the analogues, solutions for intracoronary infusion were prepared by diluting stock solutions in dimethyl sulfoxide. In such instances, solutions of adenosine used to establish a standard of potency also contained dimethyl sulfoxide.

Preparation of the complexes of analogue 18 or 19 with avidin for intracoronary infusion consisted of the dropwise addition of 1 mL of an 0.33 uM solution of 19 in dimethyl sulfoxide to a stirred solution of 20 mg (0.33 mole) of avidin in 19 mL of 0.14M NaCl. Because avidin consists of 4 subunits, each of which contains a biotin binding site, employing a 1:1 stoichiometry resulted in a fractional occupancy of 0.25. The avidin complexes were purified on columns of Sephadex G-10. The control infusate was a solution of 15 mg of avidin and 0.75 mL of dimethyl sulfoxide in 14 mL of 0.14M NaCl.

EXAMPLE

Preparation of tritiated $N^6$-[4-[[[4-[[[(2-aminoethyl)amino]carbonyl]methyl]anilino]carbonyl methyl]phenyl]adenosine (compound 16)

Unlabeled compound 16 was suspended in 0.1M sodium phosphate, pH 10, and subjected to catalytic exchange using 100 mg 5% PdO/BaSO4 under 10 Ci of tritium gas. The catalyst was removed by filtration, and labile protons were exchanged, leaving 33 mCi of radioactivity, 25% of which comigrated with ADAC by TLC (CHCl$_3$/MeoH/HOAc, 50/50/5, silica, Rf=0.14), most of the radioactive impurities were less polar than compound 16. The product (retention time 9.7 min.) was purified by HPLC using an Altex Ultrasphere ODS 5 μ column (0.46×25 cm) with a mobile phase of 50% methanol in 10 mM triethylammonium trifluoroacetate (1.0 ml/min). The recovery for the purification step was 15%. Thus, the overall yield of isolated, pure (96%) product was only 0.4%. The concentration was determined by UV spectroscopy using a value of 32,400 for the absorption peak at 303 nM. The specific activity was calculated to be 27.5 ci/mmol.

The duration of action of the larger molecular weight adenosine conjugates was prolonged relative to adenosine:

| Compound | Onset of Action | Duration of Vasodilation |
|---|---|---|
| 19 | 20–30 sec. | >1 hr. |
| 19+avidin complex | 1–2 min. | 20 min. |

IMMOBILIZED LIGANDS FOR ADENOSINE RECEPTORS

The two biotin conjugates were synthesized and described as probes for the $A_1$-adenosine receptor through avidin complexation. Based on the current results, it appears that they might be similarly useful as probes for $A_2$-receptors. The extended-chain biotin complex, 19, in particular, had a selectivity for $A_2$ receptors roughly equal to that for 2-chloroadenosine, as judged by the ratio of MPR($A_2$)/MPR($A_1$). That ratio was 54 for 2-chloroadenosine and 61 for compound 19. Thus, the biotin-avidin complex, as used for the affinity purification of insulin receptors on immobilized avidin columns is potentially applicable to the $A_2$-adenosine receptor as well as the $A_1$-receptor.

Several derivatives are designated for the covalent immobilization to solid supports for the affinity purification of adenosine receptors. The carboxylic congener may be linked to amine-functionalized polymers with water-soluble carbodiimides. Compound 8 was coupled to 6-aminohexanoic acid sepharose 4B resin (Sigma Chem. Co., St. Louis, Mo.) using ethyldimethylaminopropylcarbodiimide hydrochloride at pH 6.0. Excess amino groups were blocked by a subsequent reaction with N-succinimidyl acetate. The amino congener, 16, as immobilized efficiently by reaction with activated Sepharose resins, such as an insoluble N-hydroxysuccinimide ester (Pharmacia Activated CH Sepharose 4B) to form an amide linkage, or a carbamoylimidazole (Pierce Reactigel), to form a urethane linkage. Unreacted active acyl groups on the polymer were blocked with ethanolamine. During the immobilization reaction, the amino congener was present as the limiting reagent resulting in a 70% reaction, as indicated by UV absorption of a suspension of the polymer in a glycerol/$H_2O$ mixture (87/13, v/v). The primary amino group is also potentially reactive towards polymers functionalized with epoxy or bromoacetyl groups. The hydrazide, 15, may be linked by acylation or addition to an aldehyde, such as glutaraldehyde. The phenol bearing analogue, 17, is susceptible to electrophilic attack (reactive towards Pauly spray reagent) and thus by analogy may be linked to a diazonium functionalized polymer.

DOSAGE

The modus of administration in animals is dependent upon the animal administered to; e.g., for dogs, intramuscular, intraperitoneal, and intravenous all could be utilized, as well as oral dosages. As to dosage, a therapeutically effective dosage was administered and in this invention dosages ranging from 0.1–10 mg/kg of body weight per diem have been utilized.

We claim:

1. A method of treating a mammal to produce coronary dilation in the mammal, wherein the mammal is in need of such treatment and the method comprises administering to the mammal an adenosine compound which is selected from the group consisting of N-ethyladenosine-5'-uronamide, 2-chloroadenosine, $N^6$-methyladenosine, $N^6$-R-1-phenyl-2-propyladenosine, $N^6$-cyclohexyladenosine, $N^6$-phenyl-adenosine, and $N^6$-p-tolyladenosine.

2. The method according to claim 1, wherein the adenosine compound is N-ethyladenosine-5'-uronamide.

3. The method according to claim 1, wherein the adenosine compound is $N^6$-methyladenosine.

4. The method according to claim 1, wherein the adenosine compound is $N^6$-cyclohexyladenosine.

5. A compound of the formula:

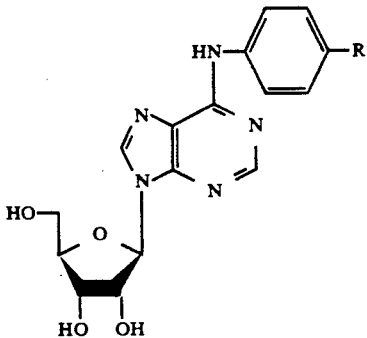

wherein,
R is

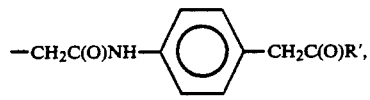

and
R' is
—$OCH_3$, —$NHCH_3$, —$NHNH_2$,

—$NH(CH_2)_2NH_2$,

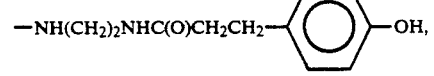

—$NH(CH_2)_2$ NHC(O)   biotin, or
—$NH(CH_2)_2NHC(O)$—$(CH_2)_5$—NHC(O) biotin.

6. A pharmaceutical composition comprising a compound of claim 5 in a pharmaceutical carrier.

7. A method of producing coronary vasodilation in a mammal in need of such vasodilation by administering to the mammal a vasodilating effective amount of a pharmaceutical composition of claim 6.

8. A compound having the formula

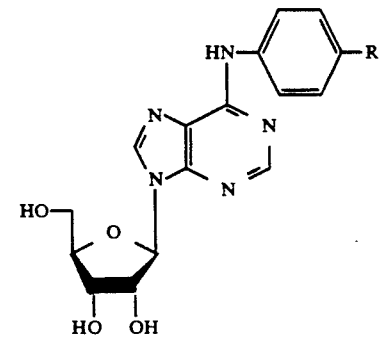

wherein,
R is —$CH_2$—C(O)—R', and

R' is hydroxyl, lower alkylamino wherein the alkyl group thereof is unsubstituted or substituted by methyl, halo-lower alkyl, lower alkyl, an ester group or an amino group; monoarylamino wherein the aryl group thereof is unsubstituted or substituted by methyl, halo-lower alkyl, lower alkyl, an ester group, or an amino group; or an oligopeptide of up to five amino acids in length in which the point of attachment is through an amide bond at the p-position of phenylalanine; or R is

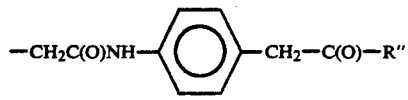

wherein R″ is alkoxy, lower alkylamino, wherein the alkyl group thereof is unsubstituted or substituted by an amino or acylamino group; or R is NH—(CH₂)₂NHR‴ wherein R‴ is an acyl moiety selected from the group consisting of acetyl, p-hydroxyphenylpropionyl, d-biotinyl, α-bromoacetyl, methyl fumaryl, d-biotinyl-ε-aminocaproyl, an amino acid of the L-configuration and an amino of the D-configuration; or R‴ is a monoaryl group; or R‴ is NH(CH₂)₂N═C═S.

9. A compound, as recited in claim 8, having the formula:

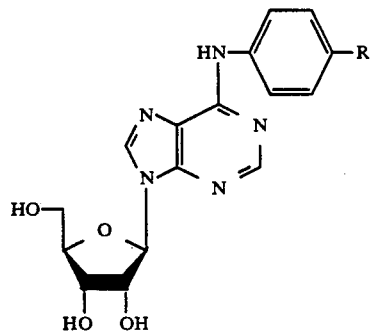

wherein:
R is —CH₂—C(O)—R' and
R' is
—OH,
—NHCH₃,
—NH—CH₂CO₂C₂H₅,

-NH-⟨phenyl-2-CH₃⟩,

-NH-⟨phenyl-3-CH₃⟩,

-continued

—NH—⟨phenyl⟩—CH₃,

—NH—⟨phenyl⟩—CF₃, or

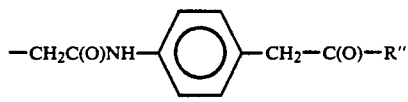

—NH—⟨phenyl⟩—CH₂CHCO₂CH₃;
                    |
                    NHCOCF₃ or

R is

—CH₂C(O)NH—⟨phenyl⟩—CH₂—C(O)—R″ and
R″ is
—OCH₃,
—NHCH₃,
—NHNH₂,
NHCH₂CH₂—NH₂,
NHCH₂CH₂—NHCOCH₃,

—NHCH₂CH₂—NHCO(CH₂)₂—⟨phenyl⟩—OH

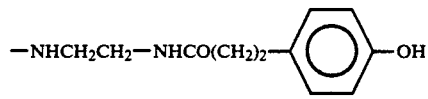

—NH(CH₂)₂NHCOCH₂Br,

—NH(CH₂)₂NH—CO—CH═CH—CO—OCH₃ (trans),

—NH(CH₂)₂N═C═S,

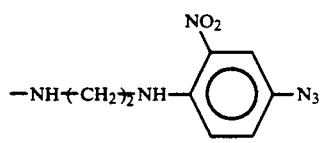

-continued $-NH(CH_2)_2NHCO(CH_2)_3NH-CO(CH_2)_4-$ [biotin-thiophene-imidazolone ring system]

or $-NH(CH_2)_2NH-CO-\underset{CH_3\ H}{C}-NH_2$

10. The compound of claim 9, which is N⁶-(4'-carboxymethyl)phenyladenosine.

11. The compound of claim 9, wherein R is —CH₂-C(O)—NHCH₃.

12. The compound of claim 9, wherein R is —CH₂-C(O)—NH—CH₂CO₂C₂H₅.

13. The compound of claim 9, wherein R is $-CH_2C(O)-NH-\bigcirc\!\!-CH_3$ (ortho)

14. The compound of claim 9, which is N⁶-(4'-carboxymethyl)phenyladenosine-p-toluide.

15. The compound of claim 9, wherein R is $-CH_2C(O)-NH-\bigcirc\!\!-CH_3$

16. The compound of claim 9, wherein R is $-CH_2C(O)-NH-\bigcirc\!\!-CF_3$

17. The compound of claim 9, which is adenosine-N⁶-(4'-carboxymethyl)phenyl-p-aminophenylacetic acid methyl ester.

18. The compound of claim 9, which is adenosine-N⁶-(4'-carboxymethyl)phenyl-p-aminophenylacetyl-N-methyl-amide.

19. The compound of claim 9, wherein R is $-CH_2C(O)NH-\bigcirc\!\!-CH_2-C(O)-NHNH_2$ 20. The compound of claim 9, which is adenosine-N⁶-(4'-carboxymethyl)phenyl-p-aminophenylacetyl-1,2-diaminoethane.

21. The compound of claim 9, wherein R is $-CH_2C(O)NH-\bigcirc\!\!-CH_2C(O)-NHCH_2CH_2NHC(O)CH_3$ 22. The compound of claim 9, wherein R is $-CH_2C(O)NH-\bigcirc\!\!-CH_2C(O)-NHCH_2CH_2NHC(O)CH_2CH_2-\bigcirc\!\!-OH$ 23. The compound of claim 9, which is adenosine-N⁶-(4'-carboxymethyl)phenyl-p-aminophenylacetyl-1,2-diaminoethane-d-biotin.

24. A pharmaceutical composition, comprising: an effective amount of a compound having the formula

[adenosine structure with HN-phenyl-R substituent at N⁶ position]

wherein
R is —CH₂C—R'; and
R' is hydroxyl, substituted or unsubstituted lower alkylamino wherein the alkyl group thereof may be substituted by methyl, halo-lower alkyl, lower alkyl, an ester group or an amino group; substituted or unsubstituted monoarylamino wherein the aryl group thereof may be substituted by methyl, halo-lower alkyl, lower alkyl, an ester group, or amino group; or an oligopeptide of up to five amino acids in length in which the point of attachment is five amino acids in length in which the point of attachment is alkyl, an ester group, or amino group; or an oligopeptide of up to five amino acids in length in which the point of attachment is through an amide bond at the p-position of phenyl-alanine; or
R is $-CH_2C(O)NH-\bigcirc\!\!-CH_2-C(O)-R''$ wherein R'' is alkoxy, lower alkylamino wherein the alkyl group thereof is unsubstituted or substituted by an amino or an acylamino group; or
R'' is NH—(CH₂)₂NHR''' wherein R''' is an acyl moiety selected from the group consisting of acetyl, p-hydroxyphenylpropionyl, d-biotinyl, α-bromoacetyl, methyl fumaryl, d-biotinyl-ε-aminocaproyl, an amino acid of the L-configuration and an amino acid of the D-configuration; or
R''' is a monoaryl group; or
R''' is NH(CH)$_2$N=C=S and a pharmaceutical carrier therefor.

25. A pharmaceutical composition as recited in claim 24, which comprises an effective amount of a compound having the formula:

wherein:
R is —CH$_2$—C(O)—R', and
R' is
—OH,
—NHCH$_3$,
—NH—CH$_2$CO$_2$C$_2$H$_5$, —NH—⌬—CH$_3$ (ortho), —NH—⌬—CH$_3$ (meta), —NH—⌬—CH$_3$ (para),

—NH—⌬—CF$_3$,

—NH—⌬—CH$_2$—CH—CONHCH$_2$CONHCH$_3$
                    |
                    NH
                    |
                    CO$_2$C(CH$_3$)$_3$ or

—NH—⌬—CH$_2$CHCO$_2$CH$_3$;
              |
              NHCOCF$_3$ or

R is

—CH$_2$C(O)NH—⌬—CH$_2$—C(O)—R'' and
R'' is
—OCH$_3$,
—NHCH$_3$,
—NHNH$_2$,
—NHCH$_2$CH$_2$—NH$_2$
—NHCH$_2$CH$_2$—NHCOCH$_3$,

—NHCH$_2$CH$_2$—NHCO—(CH$_2$)$_2$—⌬—OH,

—NHCH$_2$CH$_2$—NHCO—(CH$_2$)$_4$—[biotin ring],

—NH—(CH$_2$)$_2$NHCOCH$_2$Br,
—NH(CH$_2$)$_2$NH—CO—CH=CH—CO—OCH$_3$ (trans),
—NH(CH$_2$)$_2$N=C=S,

—NH(CH$_2$)$_2$NH—⌬(NO$_2$)—N$_3$,

—NH(CH$_2$)$_2$NHCO(CH$_2$)$_5$NH—CO(CH$_2$)$_4$—[biotin ring], or

—NH(CH$_2$)$_2$NH—CO—CH(CH$_3$)—NH$_2$;

and a pharmaceutical carrier therefor.

26. The pharmaceutical composition of claim 25, which comprises an effective amount of the compound N$^6$-(4'-carboxymethyl)-phenyladenosine.

27. The pharmaceutical composition of claim 25, which comprises an effective amount of the compound wherein R is —CH$_2$C(O)—NHCH$_3$.

28. The pharmaceutical composition of claim 25, which comprises an effective amount of the compound wherein R is —CH$_2$C(O)—NH—CH$_2$CO$_2$C$_2$H$_5$.

29. The pharmaceutical composition of claim 25, which comprises an effective amount of the compound wherein R is

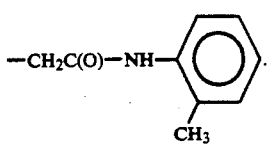

30. The pharmaceutical composition of claim 25, which comprises an effective amount of the compound $N^6$-(4'-carboxymethyl phenyl-adenosine-p-toluide.

31. The pharmaceutical composition of claim 25, which comprises an effective amount of the compound wherein R is

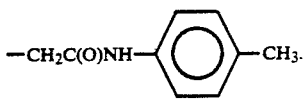

32. The pharmaceutical composition of claim 25, which comprises an effective amount of the compound wherein R is

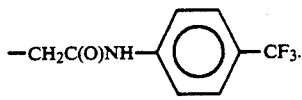

33. The pharmaceutical composition of claim 25, which comprises an effective amount of the compound adenosine-$N^6$-(4'-carboxymethyl)-phenyl-p-aminophenylacetic acid methyl ester.

34. The pharmaceutical composition of claim 25, which comprises an effective amount of the compound adenosine-$N^6$-(4'-carboxymethyl)phenyl-p-aminophenylacetyl-N-methylamide.

35. The pharmaceutical composition of claim 25, which comprises an effective amount of the compound wherein R is

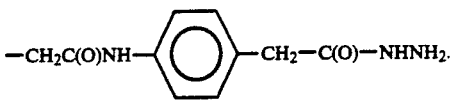

36. The pharmaceutical composition of claim 25, which comprises an effective amount of the compound adenosine-$N^6$-(4'-carboxymethyl)phenyl-p-aminophenylacetyl-1,2-diaminoethane.

37. The pharmaceutical composition of claim 25, which comprises an effective amount of the compound wherein R is

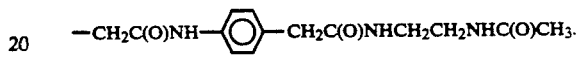

38. The pharmaceutical composition of claim 25, which comprises an effective amount of the compound wherein R is

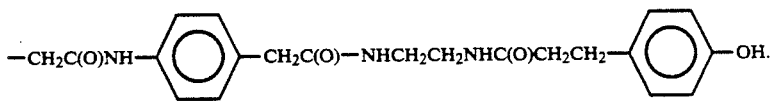

39. The pharmaceutical composition of claim 25, which comprises an effective amount of the compound adenosine-$N^6$-(4'-carboxymethyl)phenyl-p-aminophenylacetyl-1,2-diaminoethane-d-biotin.

40. A compound as recited in claim 8, wherein R' is an oligopeptide which is protected at is α-amino and α-carboxylate functionalities by conventional peptide blocking groups.

41. The pharmaceutical composition of claim 24, wherein R' is an oligopeptide which is protected at its α-amino and α-carboxylate functionalities by conventional peptide blocking groups.

42. A method of producing coronary vasodilation in a mammal in need thereof, by administering to the mammal a vasodilating effective amount of a pharmaceutical composition as recited in claim 24.

43. A method of producing coronary vasodilation in a mammal in need thereof, by administering to the mammal a vasodilating effective amount of a pharmaceutical composition as recited in claim 25.

* * * * *